United States Patent
Freeman et al.

(10) Patent No.: US 8,862,228 B2
(45) Date of Patent: Oct. 14, 2014

(54) USING CHEST VELOCITY TO PROCESS PHYSIOLOGICAL SIGNALS TO REMOVE CHEST COMPRESSION ARTIFACTS

(71) Applicant: ZOLL Medical Corporation, Chelmsford, MA (US)

(72) Inventors: Gary A. Freeman, Newton Center, MA (US); Qing Tan, Somerville, MA (US); Frederick Geheb, Danvers, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 13/872,033

(22) Filed: Apr. 26, 2013

(65) Prior Publication Data

US 2013/0245393 A1 Sep. 19, 2013

Related U.S. Application Data

(63) Continuation of application No. 10/786,359, filed on Feb. 24, 2004, now abandoned, which is a continuation-in-part of application No. 10/704,366, filed on Nov. 6, 2003, now Pat. No. 7,220,235.

(51) Int. Cl.

| | |
|---|---|
| *A61N 1/39* | (2006.01) |
| *A61B 5/04* | (2006.01) |
| *A61H 31/00* | (2006.01) |
| *A61B 5/00* | (2006.01) |
| *A61B 5/0205* | (2006.01) |
| *A61B 5/046* | (2006.01) |

(52) U.S. Cl.
CPC ...... *A61B 5/04017* (2013.01); *A61H 2201/5079* (2013.01); *A61H 2201/5084* (2013.01); *A61H 31/006* (2013.01); *A61H 2230/04* (2013.01); *A61N 1/3925* (2013.01); *A61B 5/046* (2013.01); *A61H 31/005* (2013.01); *A61H 2201/5058* (2013.01); *A61B 5/7207* (2013.01); *A61B 5/0205* (2013.01); *A61H 31/007* (2013.01)
USPC ............................................................. 607/5

(58) Field of Classification Search
USPC ............................................................. 607/5
See application file for complete search history.

(56) References Cited

U.S. PATENT DOCUMENTS

| | | |
|---|---|---|
| 3,865,101 A | 2/1975 | Saper et al. |
| 4,059,099 A | 11/1977 | Davis |

(Continued)

FOREIGN PATENT DOCUMENTS

| | | |
|---|---|---|
| EP | 1057451 | 12/2000 |
| EP | 1079310 | 2/2001 |

(Continued)

OTHER PUBLICATIONS

Aase et al., "Compression Depth Estimation for CPR Quality Assessment Using DSP on Accelerometer Signals," IEEE Transactions on Biomedical Engineering, vol. 49, No. 3, Mar. 2002.

(Continued)

*Primary Examiner* — Brian T Gedeon
(74) *Attorney, Agent, or Firm* — Fish & Richardson P.C.

(57) ABSTRACT

A method of analyzing a physiological (e.g., an ECG) signal during application of chest compressions. The method includes acquiring a physiological signal during application of chest compressions; acquiring the output of a sensor from which information on the velocity of chest compressions can be determined; and using the information on the velocity to reduce at least one signal artifact in the physiological signal resulting from the chest compressions.

21 Claims, 5 Drawing Sheets

(56) References Cited

U.S. PATENT DOCUMENTS

| | | | |
|---|---|---|---|
| 4,088,138 A | 5/1978 | Diack et al. | |
| 4,198,963 A | 4/1980 | Barkalow et al. | |
| RE30,372 E | 8/1980 | Mirowski et al. | |
| 4,296,755 A | 10/1981 | Judell | |
| 4,355,634 A | 10/1982 | Kanter | |
| 4,588,383 A | 5/1986 | Parker et al. | |
| 4,610,254 A | 9/1986 | Morgan et al. | |
| 4,619,265 A | 10/1986 | Morgan et al. | |
| 4,680,708 A | 7/1987 | Ambos et al. | |
| 4,757,821 A | 7/1988 | Snyder | |
| 4,781,200 A | 11/1988 | Baker | |
| 4,928,674 A | 5/1990 | Halperin et al. | |
| 5,077,667 A | 12/1991 | Brown et al. | |
| 5,081,993 A | 1/1992 | Kitney et al. | |
| 5,092,341 A | 3/1992 | Kelen | |
| 5,109,862 A | 5/1992 | Kelen et al. | |
| 5,193,537 A | 3/1993 | Freeman | |
| 5,211,179 A * | 5/1993 | Haberl et al. | 600/515 |
| 5,247,945 A | 9/1993 | Heinze et al. | |
| 5,285,792 A | 2/1994 | Sjoquist et al. | |
| 5,330,526 A | 7/1994 | Fincke et al. | |
| 5,348,008 A | 9/1994 | Bornn et al. | |
| RE34,800 E | 11/1994 | Hutchins | |
| 5,391,187 A | 2/1995 | Freeman | |
| 5,409,010 A | 4/1995 | Beach et al. | |
| 5,439,483 A | 8/1995 | Duong-Van | |
| 5,454,779 A | 10/1995 | Lurie et al. | |
| 5,466,244 A | 11/1995 | Morgan | |
| 5,471,991 A | 12/1995 | Shinnar | |
| 5,472,453 A | 12/1995 | Alt | |
| 5,474,574 A | 12/1995 | Payne et al. | |
| 5,496,257 A * | 3/1996 | Kelly | 601/41 |
| 5,507,778 A | 4/1996 | Freeman | |
| 5,511,553 A | 4/1996 | Segalowitz | |
| 5,562,710 A | 10/1996 | Olsen et al. | |
| 5,589,639 A | 12/1996 | D'Antonio et al. | |
| 5,591,213 A | 1/1997 | Morgan | |
| 5,611,815 A | 3/1997 | Cole et al. | |
| 5,617,853 A | 4/1997 | Morgan | |
| 5,619,265 A | 4/1997 | Suzuki et al. | |
| 5,626,140 A | 5/1997 | Feldman et al. | |
| 5,645,571 A | 7/1997 | Olson et al. | |
| 5,662,690 A | 9/1997 | Cole et al. | |
| 5,683,424 A | 11/1997 | Brown et al. | |
| 5,700,281 A | 12/1997 | Brewer et al. | |
| 5,735,879 A | 4/1998 | Gliner et al. | |
| 5,755,671 A | 5/1998 | Albrecht et al. | |
| 5,772,604 A | 6/1998 | Langberg et al. | |
| 5,782,888 A | 7/1998 | Sun et al. | |
| 5,792,190 A | 8/1998 | Olson et al. | |
| 5,957,856 A | 9/1999 | Weil et al. | |
| 5,967,995 A | 10/1999 | Shusterman et al. | |
| 6,021,349 A | 2/2000 | Arand et al. | |
| 6,125,299 A * | 9/2000 | Groenke et al. | 607/6 |
| 6,155,257 A | 12/2000 | Lurie et al. | |
| 6,171,257 B1 | 1/2001 | Weil et al. | |
| 6,174,295 B1 | 1/2001 | Cantrell et al. | |
| 6,178,357 B1 | 1/2001 | Gliner et al. | |
| 6,188,928 B1 | 2/2001 | Noren et al. | |
| 6,224,562 B1 | 5/2001 | Lurie et al. | |
| 6,246,907 B1 | 6/2001 | Lin et al. | |
| 6,263,238 B1 | 7/2001 | Brewer et al. | |
| 6,289,243 B1 | 9/2001 | Lin et al. | |
| 6,306,107 B1 | 10/2001 | Myklebust et al. | |
| 6,308,094 B1 | 10/2001 | Shusterman et al. | |
| 6,309,695 B1 * | 10/2001 | Singh | 427/103 |
| 6,334,070 B1 | 12/2001 | Nova et al. | |
| 6,351,671 B1 | 2/2002 | Myklebust et al. | |
| 6,360,125 B1 | 3/2002 | Weil et al. | |
| 6,390,996 B1 * | 5/2002 | Halperin et al. | 601/41 |
| 6,393,316 B1 | 5/2002 | Gillberg et al. | |
| 6,397,104 B1 | 5/2002 | Miller et al. | |
| 6,418,342 B1 | 7/2002 | Owen et al. | |
| 6,427,685 B1 | 8/2002 | Ray, II | |
| 6,438,419 B1 | 8/2002 | Callaway et al. | |
| 6,480,734 B1 | 11/2002 | Zhang et al. | |
| 6,496,731 B1 | 12/2002 | Lovett | |
| 6,572,547 B2 | 6/2003 | Miller et al. | |
| 6,575,914 B2 | 6/2003 | Rock et al. | |
| 6,597,943 B2 | 7/2003 | Taha et al. | |
| 6,622,042 B1 | 9/2003 | Thacker | |
| 6,658,290 B1 | 12/2003 | Lin et al. | |
| 6,671,545 B2 | 12/2003 | Fincke | |
| 6,687,540 B2 | 2/2004 | Marcovecchio | |
| 6,807,442 B1 | 10/2004 | Myklebust et al. | |
| 6,827,695 B2 * | 12/2004 | Palazzolo et al. | 601/41 |
| 7,013,176 B2 | 3/2006 | Ding et al. | |
| 7,220,235 B2 | 5/2007 | Geheb et al. | |
| 7,310,553 B2 | 12/2007 | Freeman | |
| 7,463,922 B1 | 12/2008 | Snyder et al. | |
| 7,488,293 B2 | 2/2009 | Marcovecchio et al. | |
| 7,565,194 B2 | 7/2009 | Tan et al. | |
| 7,708,683 B2 | 5/2010 | Hadley | |
| 7,831,299 B2 | 11/2010 | Tan et al. | |
| 8,165,671 B2 | 4/2012 | Freeman et al. | |
| 2001/0047140 A1 | 11/2001 | Freeman | |
| 2002/0026131 A1 | 2/2002 | Halperin | |
| 2002/0055694 A1 | 5/2002 | Halperin et al. | |
| 2002/0133197 A1 | 9/2002 | Snyder et al. | |
| 2002/0165471 A1 | 11/2002 | Halperin et al. | |
| 2002/0165585 A1 | 11/2002 | Dupelle et al. | |
| 2002/0193711 A1 | 12/2002 | Halperin et al. | |
| 2003/0055460 A1 | 3/2003 | Owen et al. | |
| 2003/0083699 A1 | 5/2003 | Hamilton et al. | |
| 2003/0195567 A1 | 10/2003 | Jayne et al. | |
| 2004/0044374 A1 | 3/2004 | Weinberg et al. | |
| 2004/0049234 A1 | 3/2004 | Morgan et al. | |
| 2004/0058305 A1 | 3/2004 | Lurie et al. | |
| 2004/0082888 A1 | 4/2004 | Palazzolo et al. | |
| 2004/0162585 A1 | 8/2004 | Elghazzawi et al. | |
| 2004/0210171 A1 | 10/2004 | Palazzolo et al. | |
| 2004/0215244 A1 | 10/2004 | Marcovecchio et al. | |
| 2005/0119706 A1 | 6/2005 | Ideker et al. | |
| 2005/0256415 A1 | 11/2005 | Tan et al. | |
| 2006/0036292 A1 | 2/2006 | Smith et al. | |
| 2006/0116724 A1 | 6/2006 | Snyder | |
| 2007/0032729 A1 | 2/2007 | Fortin | |
| 2007/0032829 A1 | 2/2007 | Ostroff | |

FOREIGN PATENT DOCUMENTS

| | | |
|---|---|---|
| EP | 1491176 | 12/2004 |
| GB | 9713345.8 | 6/1997 |
| WO | 97/24062 | 7/1997 |
| WO | 98/30282 | 7/1998 |
| WO | 99/24114 | 5/1999 |
| WO | 99/25306 | 5/1999 |
| WO | 01/56652 | 8/2001 |
| WO | 01/66182 | 9/2001 |
| WO | 02/15836 | 2/2002 |
| WO | 03/009895 | 2/2003 |
| WO | 2004/054656 | 7/2004 |
| WO | 2005/021089 | 3/2005 |

OTHER PUBLICATIONS

Aase et al., "CPR Artifact Removal from Human ECG Using Optimal Multichannel Filtering," IEEE Transactions on Biomedical Engineering, vol. 47, 1440-1449, (2000).

Afonso et al., "Detecting Ventricular Fibrillation", IEEE Engineering in Medicine and Biology, vol. 14:2, pp. 152-159 (1995).

Al-Fahoum et al., "Combined wavelet transformation and radial basis neural networks for classifying life-threatening cardiac arrhythmias", Medical & Biological Engineering & Computing, vol. 37:5, pp. 566-573 (1999).

Amann et al., Reliability of Fibrillation Detection Algorithms in Automatic External Defibrillators (AEDs), Dept. of Anaesthesia and Intensive Care Medicine, Leopold-Franzens-Universitat Innsbruck, Anichstr. 35, A-6020 Innsbruck, Austria, Dept. of Computer Science, Applied Mathematics Group, FH-Vorarlberg, Achstr. I, A-6850 Dornbirn, Austria. At the top of the paper I have is the following: Jahrestaguug der Osterreichischen Deutschen und Schweizerischen Gesellschaft fur Biomedizimische Technik Sep. 2003.

(56) References Cited

OTHER PUBLICATIONS

American Red Cross—Adult CPR/AED Training—Workplace Programs, http://www.redcross.org/hss/cpraed.html, printed from Internet May 14, 1999.
Barro et al., "Algorithmic sequential decision-making in the frequency domain for life threatening ventricular arrhythmias and imitative artifacts: a diagnostic system", J. Biomed. Eng., vol. 11:4, pp. 320-328 (1989).
Botsivaly et al., "Evaluation of a new technique for the Detection of Ventricular Fibrillation and Ventricular Tachycardia", Procs of the 22$^{nd}$ Ann EMBS Int Conf, Chicago, IL (2000).
Callaway et al., "Scaling exponent predicts defibrillation success for out-of-hospital ventricular fibrillation cardiac arrest," Circulation 103(12):1656-1661 (2001).
Callaway et al., "Ventricular Fibrillation Waveform Predicts Defibrillation Success by Automatic External Defibrillators", Academic Emergency Medicine, vol. 7:5, pp. 1-2 (2000).
Cardiac Science Brochure, Analysis Algorithm Overview, Powerheart® AED Automated External Defibrillator with RHYTHMx® Technology (no date).
Clayton et al., "Comparison of four techniques for recognition of ventricular fibrillation from the surface ECG", Medical & Biological Engineering & Computing, vol. 31:2, pp. 111-117 (1993).
Eftestol et al., "Effects of Interrupting Precordial Compressions on the Calculated Probability of Defibrillation Success During Out-of-Hospital Cardiac Arrest," Circulation, 105, 2270-2273, (2002).
Eftestøl et al., "Predicting Outcome of Defibrillation by Spectral Characterization and Nonparametric Classification of Ventricular Fibrillation in Patients With Out-of-Hospital Cardiac Arrest", Circulation, 102:1523-1529 (2000).
Efestol et al., "Probability of successful defibrillation as a monitor during CPR in out-of-hospital cardiac arrested patients," Resuscitation 48(3):245-254 (2001).
Fitzgibbon et al., "Determination of the noise source in the electrocardiogram during cardiopulmonary resuscitation", Crit Care Med, vol. 30:4, pp. S148-S152 (2002).
Flewelling, Nellcor Incorporated, Noninvasive Optical Monitoring, Chap. 88, pp. 1346-1353. CRC Press, Inc., 1995.
Force Sensing Resistors—An Overview of the Technology, FSR Integration Guide & Evaluation Parts Catalog with Suggested Electrical Interfaces (no date).
Ge et al., "Cardiac arrhythmia classification using autoregressive modeling", Biomed Eng. Online, pp. 13, (2002).
Geheb, Frederick J., "A System for the Determination of Ventricular Tachycardia or Ventricular Fibrillation during Cardio-Pulmonary Resuscitation", 2 pages (Apr. 2002).
Gruben et al., "System for Mechanical Measurements During Cardiopulmonary Resuscitation in Humans," IEEE Transactions on Biomedical Engineering, vol. 37, No. 2, Feb. 1990.
Haykin, Adaptive Filter Theory, Third Edition, Upper Saddle River, NJ, USA. Prentice-Hall, 1996.
Heartstream—The Background Our Technology, http://www.heartstream.com/techbk.htm, printed from Internet Jun. 25, 1999.
Husoy et al., "Removal of Cardiopulmonary Resuscitation Artifacts from Human ECG Using an Efficient Matching Pursuit-Like Algorithm," IEEE Transactions on Biomedical Engineering, vol. 49, 1287-1298, (2002).
Khadra et al., "Detection of life-threatening cardiac arrhythmias using the wavelet transformation", Medical & Biological Engineering & Computing, vol. 35:5, pp. 626-632 (1997).
Kuo et al., "Computer Detection of Ventricular Fibrillation", Computers in Cardiology, pp. 347-349 (Sep. 1978).
Langhelle et al. "Reducing CPR Artifacts in Ventricular Fibrillation in Vitro," Resuscitation. Mar; 48(3):279-91 (2001).
Lightfoot et al., "Dynamic nature of electrocardiographic waveform predicts rescue shock outcome in porcine ventricular fibrillation," Ann. Emerg. Med. 42(2):230-41 (Aug. 2003).
Menegazzi et al., "Immediate defibrillation versus interventions first in a swine model of prolonged ventricular fibrillation", Resuscitation, vol. 59, pp. 261-270 (2003).
Menegazzi et al., "Ventricular Fibrillation Scaling Exponent Can Guide Timing of Defibrillation and Other Therapies", Circulation, 109:926-931 (Feb. 2004).
Nygards et al., "Recognition of Ventricular Fibrillation Utilizing the Power Spectrum of the ECG", Computers in Cardiology, pp. 393-397 (1997).
Povoas et al., "Predicting the success of defibrillation by electrocardiographic analysis," Resuscitation 53(1):77-82 (2002).
Sherman et al., "Ventricular fibrillation exhibits dynamical properties and self-similarity", Resuscitation, vol. 47, pp. 163-173 (2000).
U.S. Appl. No. 10/421,652 (Marcovecchio, Optical Pulse Sensor for External Defibrillator).
U.S. Appl. No. 10/370,036 (Elghazzawi et al., CPR Sensitive ECG Analysis in an Automatic External Defibrillator).
U.S. Appl. No. 10/441,933 (Marcovecchio, Processing Pulse Signal in Conjunction with ECG Signal.
Wang et al., "Effects of Biphasic vs Monophasic Defibrillation on the Scaling Exponent in a Swine Model of Prolonged Ventricular Fibrillation", Academic Emergency Medicine, vol. 8:8, pp. 771-780 (2001).
Watson et al., "A novel wavelet transform based analysis reveals hidden structure in ventricular fibrillation", Resuscitation, vol. 43:2, pp. 121-127 (2000).
Yoji et al., "Adverse effects of interrupting precordial compression during cardiopulmonary resuscitation", Critical Care Medicine, vol. 25:5, pp. 733-736 (1997).
Yu et al., "Adverse Outcomes of Interrupted Precordial Compression During Automated Defibrillation," Circulation, 106, 368-372 (2002).
Noc et al., "Electrocardiographic Prediction of the Success of Cardiac Resuscitation," Critical Care Medicine, Williams and Wilkins Company, Baltimore, MA, US, vol. 27, No. 4, pp. 708-714(Apr. 1, 1999).
Strohmenger, "Kammerflimmern/-flattern: Pradiktoren fur den Defibrillationserfolg?" Notfall & Rettungsmedizin, vol. 6, pp. 22-26 (Feb. 1, 2003) (English Abstract).
Patterson, "Impedance cardiography: What is the source of the signal?", International Conference on Electrical Bioimpedance, Journal of Physics: Conference Series 224 (2010).

* cited by examiner

USING CHEST VELOCITY TO PROCESS PHYSIOLOGICAL SIGNALS TO REMOVE CHEST COMPRESSION ARTIFACTS

CROSS REFERENCE TO RELATED APPLICATIONS

This application is a continuation application of U.S. application Ser. No. 10/786,359, filed Feb. 24, 2004, which application is a continuation-in-part of and claims priority from U.S. application Ser. No. 10/704,366, filed on Nov. 6, 2003, now issued U.S. Pat. No. 7,220,235, and both are hereby incorporated by reference.

TECHNICAL FIELD

This invention relates to devices for assisting cardiac resuscitation.

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three (airway breathing, and circulation, including chest compressions) are combined, the term cardiopulmonary resuscitation (CPR) is used.

Current automated ECG rhythm analysis methods interrupt cardiopulmonary resuscitation (CPR) to avoid artifacts in the ECG resulting from chest compressions. Long interruptions of CPR have been shown to result in higher failure rate of resuscitation. Studies have reported that the discontinuation of precordial compression can significantly reduce the recovery rate of spontaneous circulation and the 24-hour survival rate. Y. Sato, M H. Weil, S. Sun, W. Tang, J. Xie, M. Noc, and J. Bisera, Adverse effects of interrupting precordial compression during cardiopulmonary resuscitation, Critical Care Medicine, Vol. 25(5), 733-736 (1997). Yu et al., 2002. Circulation, 106, 368-372 (2002), T. Eftestol, K. Sunde, and P A. Steen, Effects of Interrupting Precordial Compressions on the Calculated Probability of Defibrillation Success During Out-of-Hospital Cardiac Arrest, Circulation, 105, 2270-2273, (2002).

Management of breathing is another important aspect of the CPR process. Typical methods of monitoring breathing employ some form of impedance pneumography which measure and track changes in the transthoracic impedance of the patient. Currently, however, chest compressions result in significant artifact on the impedance signals, resulting in impedance-based pneumographic techniques as unreliable indicators of lung volume during chest compressions.

Adaptive filters have been attempted as a way of removing chest-compression artifacts in the ECG signal. S O. Aase, T. Eftestol, J H. Husoy, K. Sunde, and PA. Steen, CPR Artifact Removal from Human ECG Using Optimal Multichannel Filtering, IEEE Transactions on Biomedical Engineering, Vol. 47, 1440-1449, (2000). A. Langhelle, T. Eftestol, H. Myklebust, M. Eriksen, B T. Holten, P A. Steen, Reducing CPR Artifacts in Ventricular Fibrillation in Vitro. Resuscitation. March; 48(3):279-91 (2001). J H. Husoy, J. Eilevstjonn, T. Eftestol, S O. Aase, H Myklebust, and P A. Steen, Removal of Cardiopulmonary Resuscitation Artifacts from Human ECG Using an Efficient Matching Pursuit-Like Algorithm, IEEE Transactions on Biomedical Engineering, Vol 49, 1287-1298, (2002). H R. Halperin, and R D. Berger, CPR Chest Compression Monitor, U.S. Pat. No. 6,390,996 (2002). Aase et al. (2000) and Langhelle et al. (2001) used the compression depth and thorax impedance as reference signals for their adaptive filter. Husoy et al. (2002) extended this study by using a matching pursuit iteration to reduce the computational complexity; however, their results are usually computationally intensive, such as involving the calculation of a high order inverse filter. Halperin et al. (2002) proposed a frequency-domain approach using the auto- and the cross-spectrum of the signals and a time-domain approach using a recursive least square method for adaptive filtering the ECG signal. In both approaches, intensive computations are required.

There are numerous references available on adaptive filters. E.g., S. Haykin, Adaptive Filter Theory, Third Edition, Upper Saddle River, N.J., USA. Prentice-Hall, 1996

SUMMARY

In general the invention features a method of analyzing a physiological (e.g., an ECG) signal during application of chest compressions. The method includes acquiring a physiological signal during application of chest compressions; acquiring the output of a sensor from which information on the velocity of chest compressions can be determined; and using the information on the velocity to reduce at least one signal artifact in the physiological signal resulting from the chest compressions.

Preferred implementations of the invention may incorporate one or more of the following: The physiological signal may be any of a variety of physiological signals, including an ECG signal, an IPG signal, an ICG signal, or a pulse oximetry signal. The sensor may be a velocity sensor, and the information on the velocity may be determined from the velocity sensor. The sensor may be an accelerometer, and the information on the velocity may be determined from integration of the output of the accelerometer. Using the information on the velocity to reduce at least one signal artifact in the physiological signal may comprise time aligning the physiological signal with the velocity. Using the information on the velocity to reduce at least one signal artifact in the physiological signal may comprise using an adaptive filter that may be adjusted to remove chest compression artifacts. The method may include a ventricular fibrillation detection algorithm for processing the physiological signal with reduced artifact to estimate whether a ventricular fibrillation may be present. The method may include a preprocessing step that detects when chest compressions are applied and automatically initiates the adaptive filter. The method may include enabling delivery of a defibrillation shock if the algorithm estimates that ventricular fibrillation is present. A difference signal may be produced, the difference signal being representative of the difference between the physiological signal fed into the adaptive filter and the physiological signal after artifact reduction by the adaptive filter. The difference signal may provide a measure of the amount of artifact in the physiological signal. The difference signal may be used to modify the subsequent processing of the physiological signal. If the difference signal indicates that the amount of artifact exceeds a first threshold, the ventricular fibrillation detection algorithm may be modified to make it more resistant to being influenced by the artifact. If the difference signal indicates that the amount of artifact exceeds a second threshold higher than the first threshold, use of the ventricular defibrillation detection algorithm may be suspended. Spectral analysis may be performed on the difference signal, and adjustments may be made to filtering of the physiological signal based on the outcome of the spectral analysis. The velocity signal may undergo a normalization pre-processing prior to being fed to an adaptive filter. The adaptive filter may include an FIR filter. The adaptive filter may include a zero-th order filter. The adaptive filter may have coefficients that are dynamically controlled by an estimate of the physiological signal. The adaptive filter may have the capability of being automatically reset when the difference between the filter output and the measured physiological signal is beyond a threshold. The automatic reset may be capable of dynamically changing the step size and thus improving the relationship of convergence and stability of the filter. A time-aligning process may be performed on the physiological and velocity signals, wherein the time aligning process aligns the two signals relative to the compressions. The method may include adaptive filtering of the output of the time aligning process, wherein the adaptive filtering reduces the error between the physiological and velocity signals. The adaptive filter may include a Kalman filter. The adaptive filter may employ adaptive equalization.

Among the many advantages of the invention (some of which may be achieved only in some of its various implementations) are the following:

This invention provides excellent techniques for (a) adaptively removing the artifacts induced by CPR in an ECG signal, (b) enhancing an ECG signal for monitoring, and (c) increasing the reliability of ECG rhythm advisory algorithms.

As part of a rhythm advisory algorithm, various implementations of the invention could be incorporated in an ECG monitor, an external defibrillator, an ECG rhythm classifier, or a ventricular arrhythmia detector.

The invention makes it possible to continue performing CPR while ECG data is collected for an ECG rhythm advisory algorithm. This can enhance the result of CPR, leading, for example, to an increase in the success rate of resuscitation.

The invention can also provide a "cleansed" ECG signal output for display to the user of a defibrillator.

The invention also provides for the first time a means of measuring lung volume during chest compressions by impedance-based methods. The method may also be used to filter other physiological signals corrupted by compression-induced artifact, such as impedance cardiography and pulse oximetry.

This invention demonstrates excellent performance at removing the CPR artifact with a zero-th order FIR filter, thus making some implementations of the invention much simpler and faster than the adaptive-filter structures proposed in the prior art.

Pre-processing of the reference signal and an automatic-reset feature make it possible for some implementations of the invention to use a relatively large step size for adaptation, thus making convergence faster and more stable.

Some implementations of the invention achieve excellent performance in CPR-artifact removal at reduced computational cost.

Other features and advantages of the invention are described in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
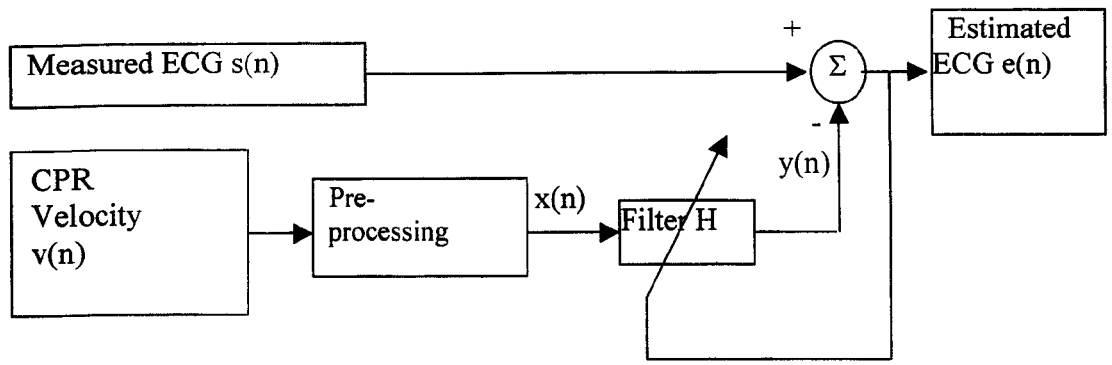
FIG. 1 is a block diagram of one implementation of the invention.

One possible implementation is illustrated by a flow chart in FIG. 1. The front end of an AED acquires both the ECG signal and the CPR signal, which is the velocity of compression of the chest. If chest displacement or acceleration are measured instead of velocity, velocity can be mathematically acquired via one or more integration or differentiation operations from the measurement signal.

The velocity signal undergoes pre-processing, and is then fed to an adaptive filter. In a preferred implementation, the pre-processing is a normalization of the velocity signal so that the signal supplied to the adaptive filter is limited to be within 0 and 1. But normalization is not required. In another implementation, a time-aligning process is performed on the ECG and the reference signal by such methods as cross-correlation. This provide alignment of the two signals relative to the compressions so that the input signals of the adaptive filter are better aligned. But this aligning process is not required. Other preprocessing can be applied to the velocity signal to improve the performance of the adaptive filter.

In FIG. 1, x(n) and y(n) are the input and the output of the adaptive filter H, which can be an FIR filter, an IIR filter, or another type of filter. In a preferred implementation, the coefficients of the filter are dynamically controlled by the estimated ECG signal:

$$h(n)=h(n-1)+m\times e(n)\times X(n)$$

where h(n) is a vector containing the filter coefficients, m is a vector containing the step sizes for each filter coefficients, e(n) is the estimated ECG signal, and X(n) is a vector containing the input data. The estimated ECG signal is computed by subtracting the filter output y(n) from the measured ECG signal (containing artifact).

In some implementations, there is an automated resetting mechanism. When the difference between the filter output y(n) and the measured ECG s(n) is beyond a threshold, the adaptive filter will reset its coefficients so that the system will not become unstable.

Other filter structures than the one shown in FIG. 1, as well as other mathematical representations of the filtering, are possible.

Figure 2:
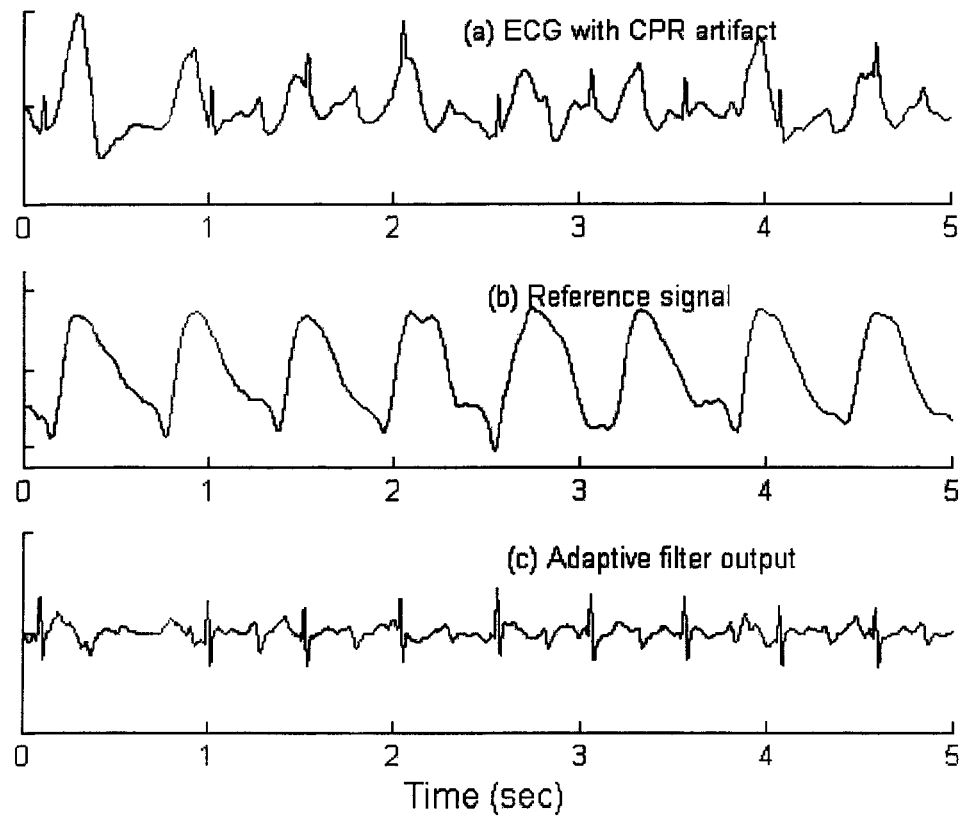
FIG. 2 shows plots of the ECG signal, CPR reference signal, and output of adaptive filter for a normal sinus rhythm.

FIG. 2 shows samples of the performance of the adaptive filter of FIG. 1 in response to a normal sinus rhythm. The signal in (a) is the ECG signal with CPR artifact. The signal in (b) is the compression velocity used as the reference signal. The signal in (c) is the output of the adaptive filter.

Figure 3:
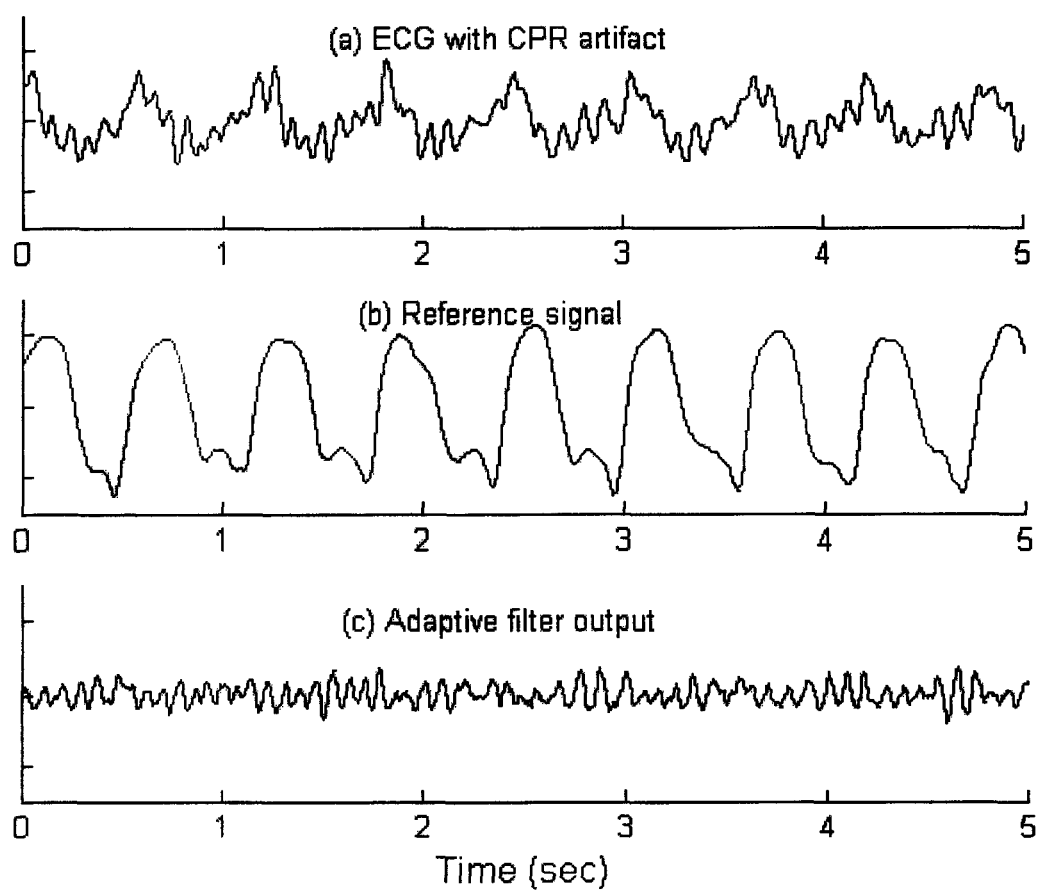
FIG. 3 shows plots of the ECG signal, CPR reference signal, and output of adaptive filter for ventricular fibrillation.

FIG. 3 shows samples of the performance of the adaptive filter of FIG. 1 during ventricular fibrillation. The signal in (a) is the ECG signal with CPR artifact. The signal in (b) is the compression velocity used as the reference signal. The signal in (c) is the output of the adaptive filter.

As shown in both FIG. 2 and FIG. 3, the implementation of FIG. 1 is able to suppress the CPR artifacts embedded in the measured ECG signals (a). The CPR artifact is nearly, if not completely, removed in the estimated ECG signal (c). The velocity signal (b) used as a reference signal is clearly correlated with the CPR artifacts in the measured ECG signals (a).

The adaptive filter assumes that the artifact in the signal is correlated with the reference signal and uncorrelated with the desired signal (estimated ECG). It thus adaptively estimates the artifact using the reference signal and subtracts the estimated artifact from the measured ECG signal.

The results shown in FIG. 2 are based on a 0th-order FIR filter, which simply scales the current sample of the ECG signal adaptively. The CPR artifact was significantly reduced, if not completely removed. This implementation thus combines simplicity and efficiency in its performance.

In the applications of adaptive filters, the speed of adaptation convergence is usually controlled by a step-size variable. A faster convergence requires a larger step size, which usually tends to make the filter less stable. The automatic resetting mechanism of some implementations can dynamically change the step size and thus improve the relation of convergence and stability.

The coefficients of the filter are updated in a sample-by-sample manner. The changes of the coefficients, i.e., h(n)-h(n−1) is proportional to the product of the step size and the reference signal. The amplitude of the reference signal can thus affect the stability and convergence of the filter. The pre-processing of the reference signal can therefore enhance the performance of the filter by adjusting the reference signal.

In another implementation, a time-aligning process is performed on the ECG and velocity signals by such methods as cross-correlation. This provide alignment of the two signals relative to the compressions. Then, preferably, adaptive filtering methods are used such as those involved in the minimization of the mean-squared error between the ECG and the velocity.

A processing unit could be provided for detecting when compressions are being applied and automatically turning on the adaptive filter. The output of the adaptive filter (i.e., the ECG signal with artifact reduced) could be supplied to a ventricular fibrillation (VF) detection algorithm (e.g., a shock advisory algorithm) of an automatic external defibrillator (AED).

An error signal could be produced that is representative of the difference between the ECG input and ECG output of the adaptive filter. This error signal would give a measure of the amount of CPR artifact in the signal, and it would be useful as a means of modifying the subsequent processing of the ECG. For instance, if the artifact level gets high enough (e.g., higher than a first threshold), the VF detection algorithm thresholds could be increased to make it more resistant to any CPR artifact that still remained in the ECG signal. If the level got even higher (e.g., higher than a second threshold higher than the first threshold), the VF detection could be shut off entirely.

In preferred implementation, the filter output is presented graphically on the display of a defibrillator or other medical device incorporating an electro-cardiographic function. The filter output may also be printed on a strip-chart recorder in the medical device. Alternatively, the filter output may provide the input signal for subsequent signal processing performed by the processing means. The purpose of such signal processing may take the form of QRS detection, paced beat detection during pacing, arrhythmia analysis, and detection of ventricular fibrillation or other shockable rhythms.

Spectral analysis could be performed on the error signal, and based on the major bands of frequency content of the error signal, the pre-filtering of the ECG signal prior to the VF detection can be adjusted. For instance, if the error signal is found to reside primarily in the 3-5 Hz band, additional filtering can be provided in that band prior to input into the VF detection (or other ECG processing) algorithm.

Many other implementations of the invention other than those described above are within the invention, which is defined by the following claims.

For example, methods of adaptive channel equalization may be employed to ameliorate both synchronization and phase errors in the velocity waveform. Kalman filtering techniques may also be employed to improve performance of the filter when rescuer performance of chest compressions changes over time and is better modeled as a non-stationary process.

Time alignment of the ECG and velocity signal may also be accomplished by such methods as cross-correlation techniques known to those skilled in the art. This will provide alignment of the two signals relative to the compressions. Then, preferably, adaptive filtering methods are used such as those involved in the minimization of the mean-squared error between the ECG and the velocity.

Figure 4:
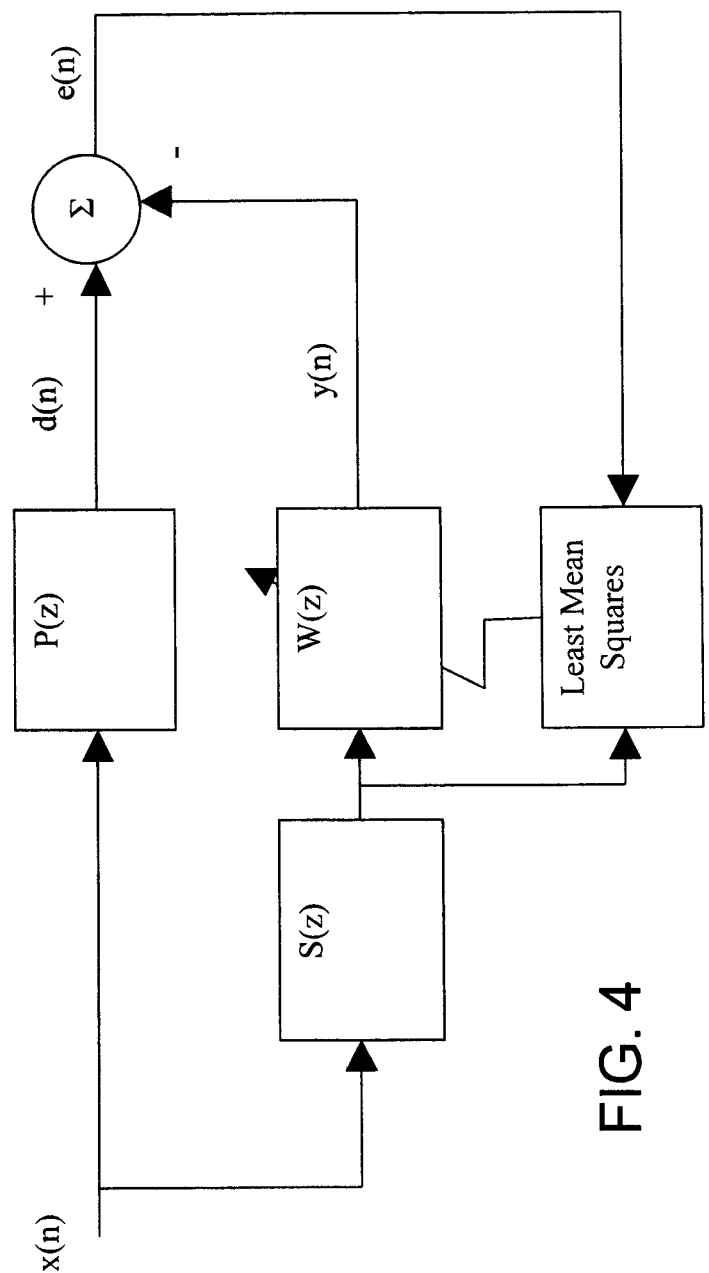
FIG. 4 is a block diagram of a filtered-X least mean squares (FXLMS ANC) algorithm.
Figure 5:
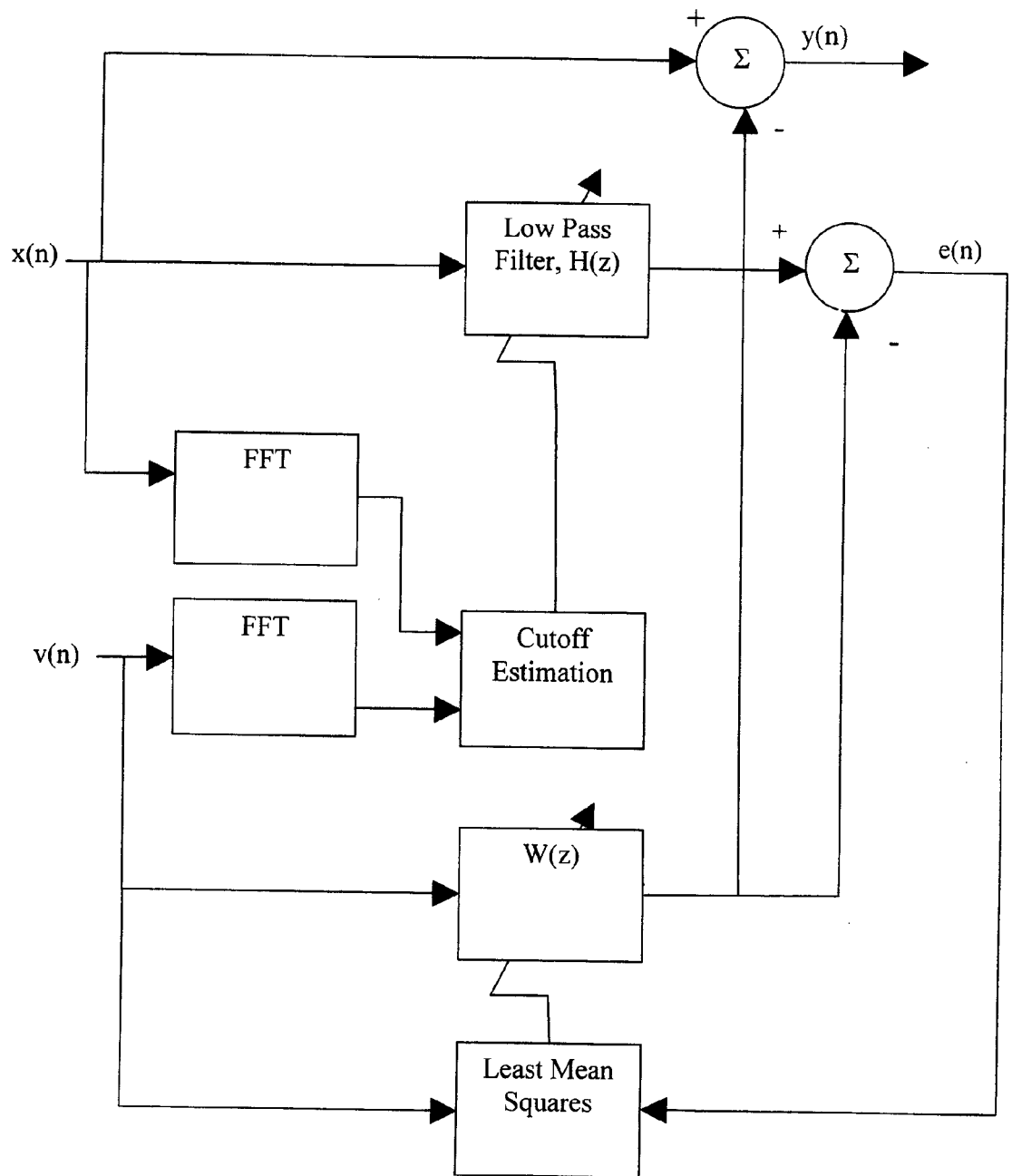
FIG. 5 is a block diagram of an implementation using the algorithm of FIG. 4.
Figure 6:
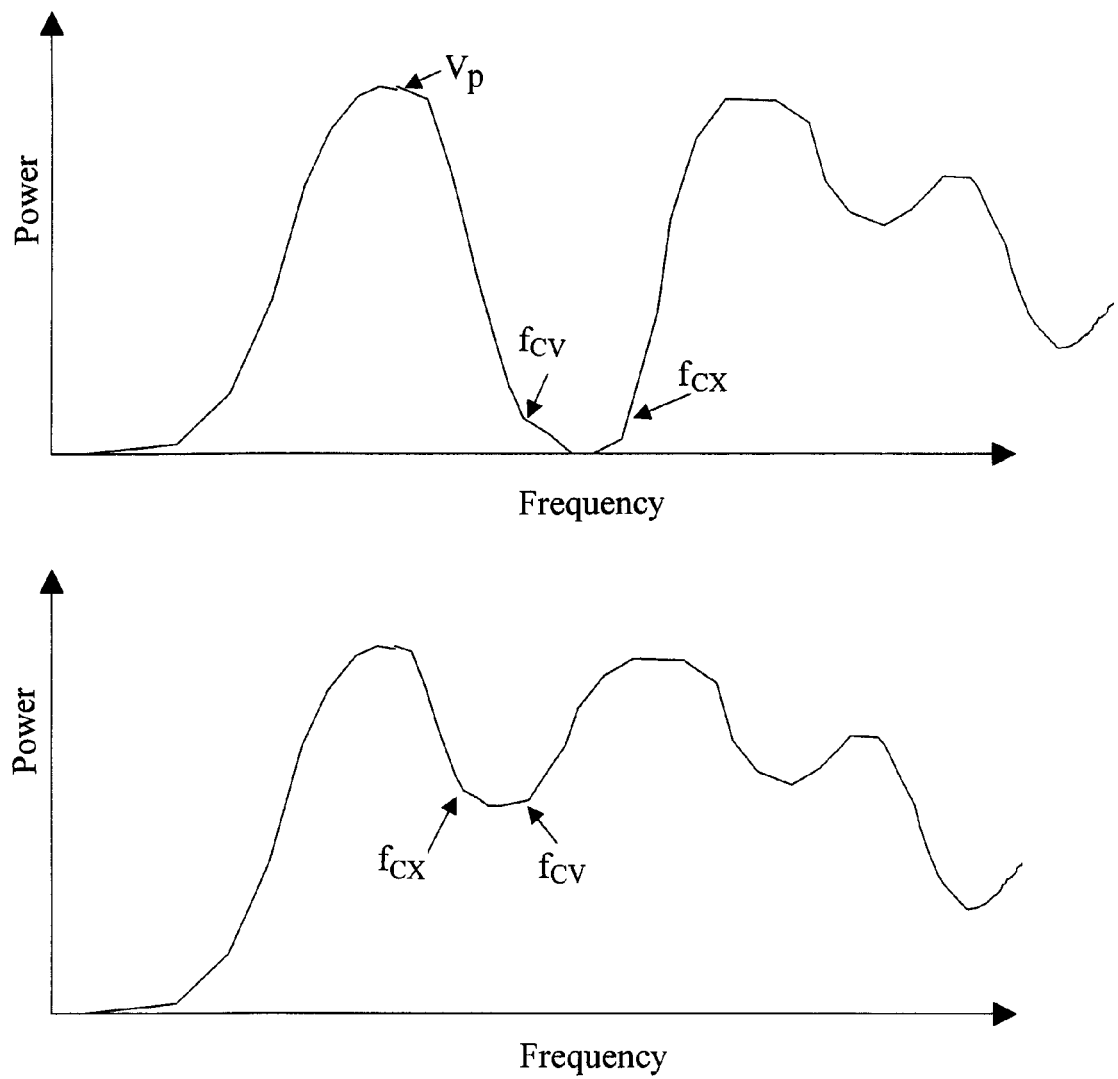
FIG. 6 shows two spectral power distributions related to the implementation of FIG. 5.

In a further implementation, more sophisticated signal processing methods may be used to minimize ECG artifacts induced by CPR chest compressions. For example, methods known as feed forward active noise cancellation (FANC) may be used. FIG. 4 shows a block diagram of the filtered-X least mean squares (FXLMS ANC) algorithm, as developed by Widrow and Burgess. P(z) represents the unknown plant through which the signal x(n) is filtered. Digital filter W(z) is adaptively adjusted to minimize the error signal e(n). In one implementation, as depicted in FIG. 5, x(n) is the unfiltered ECG signal, P(z) is eliminated from the diagram, and d(n) is approximated with the chest compression velocity signal v(n). In the LMS algorithm, assuming a mean square cost function $\xi(n)=E[e2(n)]$, the adaptive filter minimizes the instantaneous squared error, $\xi(n)=e2(n)$, using the steepest descent algorithm, which updates the coefficient vector in the negative gradient direction with step size μ:

$$w(n+1)=w(n)-\mu/2*\tilde{N}\xi(n),$$

where $\tilde{N}\xi(n)$ is an instantaneous estimate of the mean square error (MSE) gradient at time n equal to −2v(n) e(n). Stability and accuracy of the FXLMS ANC algorithm can be improved by adding a variable cutoff low pass filter H(z) to eliminate frequency components in the ECG not related to the chest compression artifact. In general, the spectral energy of the chest compression artifact is predominately lower than those of the ECG. A cutoff frequency of approximately 3 Hz is adequate in many cases, but this may vary from patient to patient and among different rescuers performing chest compressions. To overcome this difficulty, an FFT is performed on v(n) and input into a cutoff frequency estimation (CFE) procedure that determines the optimal cutoff frequency, fC, for the lowpass filter. In a preferred implementation, the decision is based on calculating the frequency, not to exceed 5 Hz, below which 80% of the waveform energy is present, but this percentage may vary and additional decision logic may be employed. For instance, an FFT may also be calculated for x(n), also input to the CFE procedure. By first normalizing amplitude of the frequency spectra X(z) amplitude peak of the compression artifact and then subtracting the velocity spectra V(z) from the normalized input X'(z), the difference spectra is calculated $\Delta X'(z)=X'(z)-V'(z)$. Frequencies are then determined for V(z) and $\Delta X'(z)$ at which most of the spectral energy is within, set in this embodiment to 97%, and labeled fCV and fCX, respectively, and shown in FIG. 6. FC is then set to the lesser of fCV and fCX. Alternatively, fC can be set to some intermediate frequency between fCV and fCX.

The quality of other physiological signals, such as impedance cardiographic (ICG), impedance pneumographic (IPG), or pulse oximetry, known to those skilled in the art, may also be also be enhanced by the filter, particularly if the sensor is located on the thoracic cage in nearby proximity to the motion sensor from which the velocity signal is derived. Minimization of compression artifact with impedance pneumography signals can be accomplished with any of the previously described methods.

The adaptive filter can be used to minimize the cross-correlation of the adaptive-filter output with the reference signal or the cross-correlation of the adaptive-filter output with the measured ECG signal.

The invention claimed is:

1. A device for analyzing an impedance cardiographic (ICG) physiological signal during application of chest compressions, the device comprising:
   circuitry for acquiring a impedance cardiographic physiological signal from a impedance cardiographic sensor applied to the chest during application of chest compressions;
   circuitry for acquiring the output of a motion sensor applied to the chest from which information on the velocity of chest compressions can be determined, and
   processing circuitry for using the information on the velocity to reduce at least one signal artifact in the impedance cardiographic signal resulting from the chest compressions.

2. A device for analyzing an impedance pneumographic physiological signal during application of chest compressions, the device comprising:
   circuitry for acquiring a impedance pneumographic physiological signal from a impedance pneumographic sensor applied to the chest during application of chest compressions;
   circuitry for acquiring the output of a motion sensor applied to the chest from which information on the velocity of chest compressions can be determined, and
   processing circuitry for using the information on the velocity to reduce at least one signal artifact in the impedance pneumographic signal resulting from the chest compressions.

3. The device of claim 1 or 2 wherein the motion sensor is a velocity sensor, and the information on the velocity is determined from the velocity sensor.

4. The device of claim 1 or 2 wherein the motion sensor is an accelerometer, and the information on the velocity is determined from integration of the output of the accelerometer.

5. The device of claim 1 or 2 wherein using the information on the velocity to reduce at least one signal artifact in the physiological signal comprises time aligning the physiological signal with the velocity.

6. The device of claim 1 or 2 wherein using the information on the velocity to reduce at least one signal artifact in the physiological signal comprises using an adaptive filter that is adjusted to remove chest compression artifacts.

7. The device of claim 6 wherein the processing circuitry is configured to provide a preprocessing step that detects when chest compressions are applied and automatically initiates the adaptive filter.

8. The device of claim 6 wherein the processing circuitry is configured to produce a difference signal, the difference signal being representative of the difference between the physiological signal fed into the adaptive filter and the physiological signal after artifact reduction by the adaptive filter.

9. The device of claim 8 wherein the difference signal provides a measure of the amount of artifact in the physiological signal.

10. The device of claim 9 the difference signal is used to modify the subsequent processing of the physiological signal.

11. The device of claim 10 wherein spectral analysis is performed on the difference signal, and adjustments are made to filtering of the physiological signal based on the outcome of the spectral analysis.

12. The device of claim 6 wherein the velocity signal undergoes a normalization pre-processing prior to being fed to an adaptive filter.

13. The device of claim 6 wherein the adaptive filter comprises an FIR filter.

14. The device of claim 13 wherein the adaptive filter comprises a zero-th order filter.

15. The device of claim 6 wherein the adaptive filter comprises coefficients that are dynamically controlled by an estimate of the physiological signal.

16. The device of claim 6 wherein the adaptive filter comprises the capability of being automatically reset when the difference between the filter output and the measured physiological signal is beyond a threshold.

17. The device of claim 16 wherein the automatic reset comprises the capability of dynamically changing the step size and thus improving the relationship of convergence and stability of the filter.

18. The device of claim 1 or 2 further comprising a time-aligning process performed on the physiological and velocity signals, wherein the time aligning process aligns the two signals relative to the compressions.

19. The device of claim 18 further comprising adaptive filtering of the output of the time aligning process, wherein the adaptive filtering reduces the error between the physiological and velocity signals.

20. The device of claim 6 wherein the adaptive filter comprises a Kalman filter.

21. The device of claim 6 wherein the adaptive filter employs adaptive equalization.

* * * * *